(12) United States Patent
Hooven et al.

(10) Patent No.: US 10,729,842 B2
(45) Date of Patent: Aug. 4, 2020

(54) MEDICAL VIAL AND INJECTOR ASSEMBLIES AND METHODS OF USE

(71) Applicant: Enable Injections, Inc., Cincinnati, OH (US)

(72) Inventors: Michael D. Hooven, Cincinnati, OH (US); Matthew J. Huddleston, Loveland, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 102 days.

(21) Appl. No.: 15/481,753

(22) Filed: Apr. 7, 2017

(65) Prior Publication Data

US 2017/0209642 A1    Jul. 27, 2017

Related U.S. Application Data

(63) Continuation of application No. 14/423,938, filed as application No. PCT/US2013/059359 on Sep. 12, 2013, now abandoned.
(Continued)

(51) Int. Cl.

| A61M 5/00 | (2006.01) |
|---|---|
| A61J 1/14 | (2006.01) |
| A61M 5/24 | (2006.01) |
| A61M 5/32 | (2006.01) |
| A61M 5/14 | (2006.01) |
| A61M 5/142 | (2006.01) |

(Continued)

(52) U.S. Cl.
CPC ............... *A61M 5/00* (2013.01); *A61J 1/14* (2013.01); *A61M 5/14* (2013.01); *A61M 5/142* (2013.01); *A61M 5/145* (2013.01); *A61M 5/148* (2013.01); *A61M 5/14248* (2013.01); *A61M 5/152* (2013.01); *A61M 5/2459* (2013.01); *A61M 5/32* (2013.01)

(58) Field of Classification Search
CPC ........ A61M 5/152; A61M 2005/14252; A61M 5/2425; A61M 5/282; A61J 1/22
See application file for complete search history.

(56) References Cited

U.S. PATENT DOCUMENTS

| 2,584,397 A | 2/1952 | Pitman |
| 2,737,948 A | 3/1956 | Brown |

(Continued)

FOREIGN PATENT DOCUMENTS

| EP | 0699090 | 3/1996 |
| EP | 0709104 B1 | 3/1998 |

(Continued)

OTHER PUBLICATIONS

PCT International Search Report for PCT/US2013/059359 dated Dec. 18, 2013.
(Continued)

*Primary Examiner* — Emily L Schmidt
(74) *Attorney, Agent, or Firm* — Cook Alex Ltd.; R. Blake Johnston

(57) ABSTRACT

A medical liquid vial is disclosed with a resilient inner bladder and a pre-stress member located with the bladder. Injector assemblies are also disclosed for injecting the vial contents into a patient by advancing the vial through a series of stages or positions. Methods of filling and use are also disclosed.

13 Claims, 16 Drawing Sheets

Related U.S. Application Data

(60) Provisional application No. 61/704,922, filed on Sep. 24, 2012.

(51) Int. Cl.
    *A61M 5/145*     (2006.01)
    *A61M 5/148*     (2006.01)
    *A61M 5/152*     (2006.01)

(56) References Cited

U.S. PATENT DOCUMENTS

| | | |
|---|---|---|
| 2,941,531 A | 6/1960 | Stevens |
| 3,016,895 A | 1/1962 | Sein |
| 3,089,491 A | 5/1963 | Mirow |
| 3,343,538 A | 9/1967 | Morley |
| 3,608,550 A | 9/1971 | Stawski |
| 3,938,520 A | 2/1976 | Scislowicz et al. |
| 3,941,171 A | 3/1976 | Ogle |
| 3,993,069 A | 11/1976 | Buckles et al. |
| 4,031,889 A | 6/1977 | Pike |
| 4,201,207 A | 5/1980 | Buckles et al. |
| 4,337,769 A | 7/1982 | Olson |
| 4,386,929 A | 6/1983 | Peery et al. |
| 4,387,833 A | 6/1983 | Venus |
| 4,419,096 A | 12/1983 | Leeper et al. |
| 4,525,164 A | 6/1985 | Loeb et al. |
| 4,537,593 A | 8/1985 | Alchas |
| 4,543,101 A | 9/1985 | Crouch |
| 4,564,054 A | 1/1986 | Gustavsson |
| 4,583,971 A | 4/1986 | Bocquet et al. |
| 4,619,651 A | 10/1986 | Kopfer et al. |
| 4,671,328 A | 6/1987 | Mueller |
| 4,702,397 A | 10/1987 | Gortz |
| 4,734,092 A | 3/1988 | Millerd |
| 4,743,243 A | 5/1988 | Vaillancourt |
| 4,823,623 A | 4/1989 | Carpenter et al. |
| 4,886,495 A | 12/1989 | Reynolds |
| 4,886,499 A | 12/1989 | Cirelli et al. |
| 5,011,477 A | 4/1991 | Winchell et al. |
| 5,045,064 A | 9/1991 | Idriss |
| 5,122,116 A | 6/1992 | Kriesel et al. |
| 5,167,641 A | 12/1992 | Schmitz |
| 5,226,900 A | 7/1993 | Bancsi et al. |
| 5,263,935 A * | 11/1993 | Hessel .............. A61M 5/152 128/DIG. 12 |
| 5,298,023 A | 3/1994 | Haber et al. |
| 5,298,025 A | 3/1994 | Hessel et al. |
| 5,329,976 A | 7/1994 | Haber et al. |
| 5,360,410 A | 11/1994 | Wacks |
| 5,411,499 A | 5/1995 | Dudar et al. |
| 5,429,607 A | 7/1995 | McPhee |
| 5,466,220 A | 11/1995 | Brenneman |
| 5,503,628 A | 4/1996 | Fetters et al. |
| 5,527,288 A * | 6/1996 | Gross .............. A61M 5/14248 604/140 |
| 5,616,132 A | 4/1997 | Newman |
| 5,636,660 A | 6/1997 | Pfleiderer et al. |
| 5,858,001 A | 1/1999 | Tsals et al. |
| 5,954,695 A | 9/1999 | Sims et al. |
| 5,957,895 A | 9/1999 | Sage |
| 5,989,237 A | 11/1999 | Fowles et al. |
| 6,045,534 A | 4/2000 | Jacobsen et al. |
| 6,113,583 A | 9/2000 | Fowles et al. |
| 6,293,159 B1 | 9/2001 | Kriesel et al. |
| 6,364,865 B1 | 4/2002 | Lavi et al. |
| 6,478,771 B1 | 11/2002 | Lavi et al. |
| 6,571,837 B2 | 6/2003 | Jansen et al. |
| 6,641,565 B1 | 11/2003 | Levi et al. |
| 6,645,181 B1 | 11/2003 | Lavi et al. |
| 6,719,719 B2 | 4/2004 | Carmel et al. |
| 6,723,068 B2 | 4/2004 | Lavi et al. |
| 6,790,199 B1 | 9/2004 | Gianakos |
| 6,948,552 B2 | 9/2005 | Newbrough et al. |
| 6,960,192 B1 | 11/2005 | Flaherty |
| 6,986,760 B2 | 1/2006 | Giambattista et al. |
| 7,214,221 B2 | 5/2007 | Fentress et al. |
| 7,491,197 B2 | 2/2009 | Jansen et al. |
| 7,540,858 B2 | 6/2009 | DiBiasi |
| 7,637,891 B2 | 12/2009 | Wall |
| 7,670,314 B2 | 3/2010 | Wall et al. |
| 7,815,609 B2 | 10/2010 | Hines |
| D631,153 S | 1/2011 | McGlothlin et al. |
| 7,882,863 B2 | 2/2011 | Pestotnik |
| 7,927,306 B2 | 4/2011 | Cross |
| 7,938,801 B2 | 5/2011 | Hawkins |
| 7,955,297 B2 | 6/2011 | Radmer et al. |
| 7,959,600 B2 | 6/2011 | Chang et al. |
| 7,981,076 B2 | 7/2011 | Sullivan et al. |
| 8,070,739 B2 | 12/2011 | Zinger et al. |
| 8,100,853 B2 | 1/2012 | Glynn |
| 8,110,209 B2 | 2/2012 | Prestrelski et al. |
| 8,123,725 B2 | 2/2012 | Carr |
| 8,142,414 B2 | 3/2012 | Patrick et al. |
| 8,147,477 B2 | 4/2012 | Smith et al. |
| 8,162,923 B2 | 4/2012 | Adams |
| 8,186,511 B2 | 5/2012 | Timm |
| 8,317,743 B2 | 11/2012 | Denenburg |
| 8,348,898 B2 | 1/2013 | Cabiri |
| 8,444,604 B2 | 5/2013 | Cindrich et al. |
| 8,480,623 B2 | 7/2013 | Mernoe et al. |
| 8,523,814 B2 | 9/2013 | Finke |
| 8,529,502 B2 | 9/2013 | Radmer |
| RE44,640 E | 12/2013 | Heiniger |
| 8,597,270 B2 | 12/2013 | Kavazov |
| 8,758,299 B2 | 6/2014 | Sadowski et al. |
| 8,894,612 B2 | 11/2014 | Hawkins et al. |
| 2002/0004648 A1 | 1/2002 | Larsen et al. |
| 2002/0123719 A1 | 9/2002 | Lavi et al. |
| 2003/0060776 A1 | 3/2003 | Heiniger |
| 2004/0015134 A1 | 1/2004 | Lavi et al. |
| 2004/0024211 A1 | 2/2004 | Boyce et al. |
| 2004/0030285 A1 | 2/2004 | Lavi et al. |
| 2004/0069044 A1 | 4/2004 | Lavi et al. |
| 2004/0116847 A1 * | 6/2004 | Wall .............. A61K 9/0019 604/93.01 |
| 2004/0138612 A1 | 7/2004 | Shermer et al. |
| 2004/0210197 A1 | 10/2004 | Conway |
| 2005/0177117 A1 | 8/2005 | Crocker et al. |
| 2006/0018941 A1 | 1/2006 | Matsuda et al. |
| 2006/0122577 A1 | 6/2006 | Poulsen et al. |
| 2007/0078415 A1 | 4/2007 | Jakobsen |
| 2007/0088252 A1 | 4/2007 | Pestotnik et al. |
| 2007/0244457 A1 | 10/2007 | Fangrow |
| 2007/0255262 A1 | 11/2007 | Haase |
| 2007/0276320 A1 | 11/2007 | Wall et al. |
| 2007/0282269 A1 | 12/2007 | Carter |
| 2008/0154200 A1 | 6/2008 | Lesch |
| 2008/0215015 A1 | 9/2008 | Cindrich et al. |
| 2008/0312600 A1 | 12/2008 | Krulevitch et al. |
| 2009/0118669 A1 | 5/2009 | Bendek et al. |
| 2009/0145509 A1 | 6/2009 | Baker et al. |
| 2009/0163866 A1 | 6/2009 | Hines et al. |
| 2009/0247953 A1 | 10/2009 | Yeshurun et al. |
| 2009/0281497 A1 | 11/2009 | Kamen et al. |
| 2009/0326457 A1 | 12/2009 | O'Connor |
| 2010/0030181 A1 | 2/2010 | Helle et al. |
| 2010/0036318 A1 | 2/2010 | Raday et al. |
| 2010/0087786 A1 | 4/2010 | Zinger |
| 2010/0130958 A1 | 5/2010 | Kang et al. |
| 2010/0179473 A1 | 7/2010 | Genosar |
| 2010/0185177 A1 | 7/2010 | Gillum |
| 2010/0185178 A1 | 7/2010 | Sharp et al. |
| 2010/0312220 A1 | 12/2010 | Kalitzki |
| 2010/0331773 A1 | 12/2010 | Frederiksen et al. |
| 2011/0004183 A1 | 1/2011 | Carrez et al. |
| 2011/0021905 A1 | 1/2011 | Patrick et al. |
| 2011/0023997 A1 | 2/2011 | Scholten et al. |
| 2011/0098657 A1 | 4/2011 | Jennings |
| 2011/0108158 A1 | 5/2011 | Huwiler et al. |
| 2011/0184348 A1 | 7/2011 | Bates et al. |
| 2011/0213299 A1 | 9/2011 | Cronenberg |
| 2011/0301548 A1 | 12/2011 | Young |
| 2011/0306929 A1 | 12/2011 | Levesque et al. |

(56) References Cited

U.S. PATENT DOCUMENTS

| | | |
|---|---|---|
| 2012/0041367 A1 | 2/2012 | Cronenberg et al. |
| 2012/0067429 A1 | 3/2012 | Mosler et al. |
| 2012/0089088 A1 | 4/2012 | Foshee et al. |
| 2012/0150139 A1 | 6/2012 | Studer |
| 2012/0157965 A1 | 6/2012 | Wotton et al. |
| 2012/0184902 A1 | 7/2012 | Jeter et al. |
| 2013/0018326 A1 | 1/2013 | Hooven |
| 2013/0116624 A1 | 5/2013 | Plunnecke |
| 2013/0218123 A1 | 8/2013 | Belriger |
| 2013/0261558 A1 | 10/2013 | Hourmand et al. |
| 2013/0296807 A1 | 11/2013 | Lintern |
| 2013/0313156 A1 | 11/2013 | Duncan |
| 2013/0324884 A1 | 12/2013 | Hadvary |
| 2014/0008366 A1 | 1/2014 | Genosar |
| 2015/0141922 A1 | 5/2015 | Tefera |
| 2015/0148772 A1 | 5/2015 | Tefera |

FOREIGN PATENT DOCUMENTS

| | | |
|---|---|---|
| EP | 0706805 B1 | 11/1998 |
| EP | 0988868 A1 | 3/2000 |
| EP | 1070230 A1 | 1/2001 |
| EP | 1039947 A4 | 6/2001 |
| EP | 0636035 B1 | 10/2001 |
| EP | 2659921 A2 | 11/2013 |
| EP | 2803348 A1 | 11/2014 |
| EP | 2337543 B1 | 12/2014 |
| JP | 09-201396 A | 8/1997 |
| WO | WO 96/39213 A1 | 12/1996 |
| WO | WO 97/20536 A1 | 6/1997 |
| WO | WO 97/41917 A1 | 11/1997 |
| WO | WO 99/26581 A1 | 6/1999 |
| WO | WO 99/30759 A2 | 6/1999 |
| WO | WO 00/29049 A1 | 5/2000 |
| WO | WO 01/76684 A1 | 10/2001 |
| WO | WO 2004/024211 A2 | 3/2004 |
| WO | WO 2004/024211 A3 | 3/2004 |
| WO | WO 2005/079440 A2 | 9/2005 |
| WO | WO 2005/079440 A3 | 9/2005 |
| WO | WO 2005/079441 A2 | 9/2005 |
| WO | WO 2005/079441 A3 | 9/2005 |
| WO | WO 2011/123659 A1 | 10/2011 |
| WO | WO 2014/204894 A2 | 12/2014 |
| WO | WO 2015/015379 A1 | 2/2015 |
| WO | WO 2015/028458 A1 | 3/2015 |
| WO | WO 2015/094945 A1 | 6/2015 |
| WO | WO 2015/164649 A1 | 10/2015 |

OTHER PUBLICATIONS

PCT Written Opinion of the International Searching Authority for PCT/US2013/059359 dated Dec. 18, 2013.
PCT International Preliminary Report on Patentability for PCT/US2013/059359 dated Mar. 24, 2015.
European Supplementary Search Report and European Search Opinion for EP Application No. 11763443.6 (published as EP 2552518) dated Apr. 4, 2014.
Notification of Transmittal of the International Search Report, International Search Report and Written Opinion for PCT/US2011/030748 dated Jun. 6, 2011.
PCT International Preliminary Report on Patentability and Written Opinion for PCT/US2011/030748 dated Oct. 11, 2012.
International Search Report for International Application No. PCT/US2014/042627 dated May 29, 2015.
Written Opinion of the International Searching Authority for International Application No. PCT/US2014/042627 dated May 29, 2015.
Two-page Brochure of Neria—Multi Infusion Sets by Unomedical Company.
European Supplemental Search Report for EP Application No. 98964008 (as published EP1039947) dated Jan. 31, 2001.

\* cited by examiner

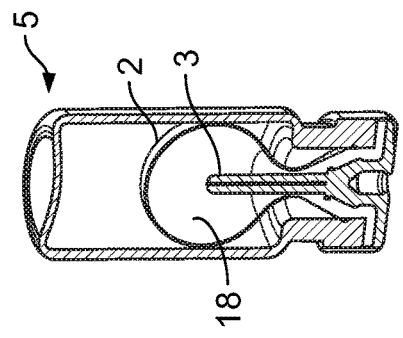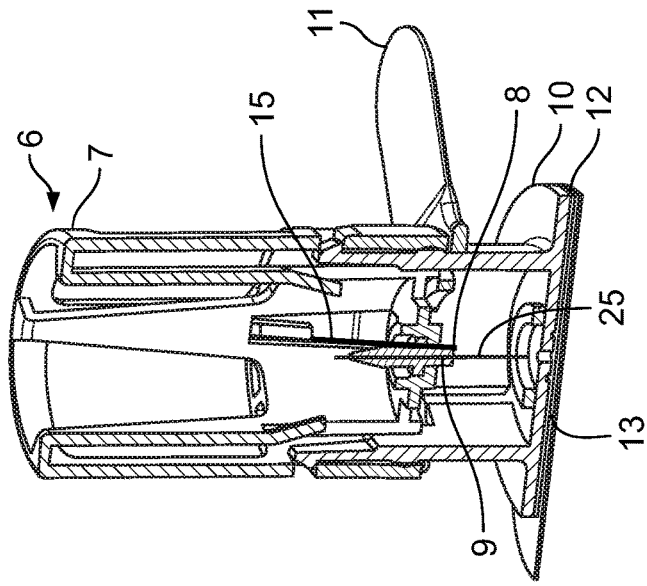
FIGURE 6
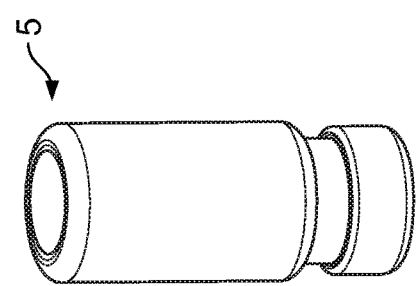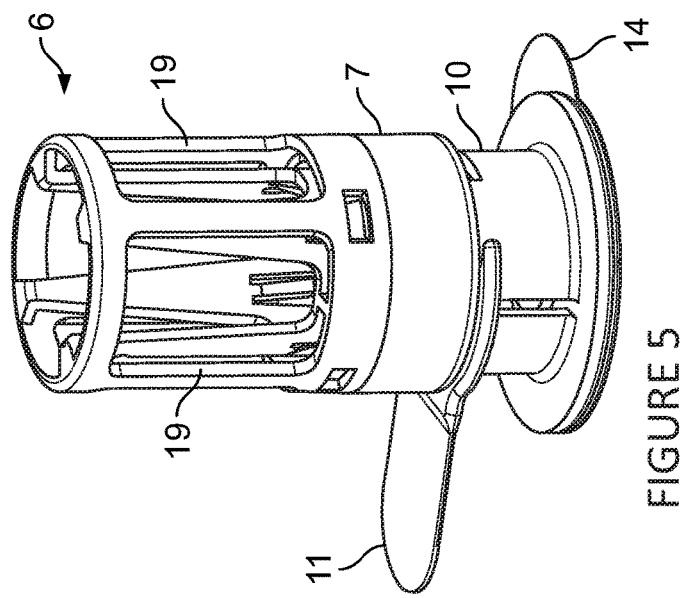
FIGURE 5

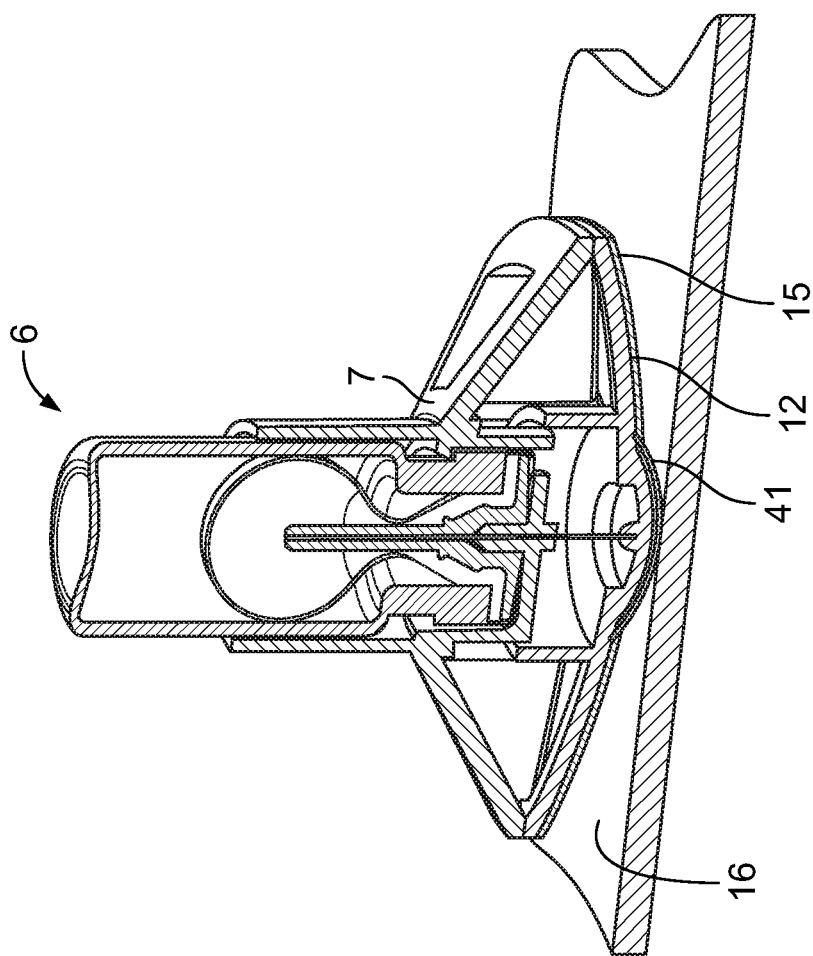
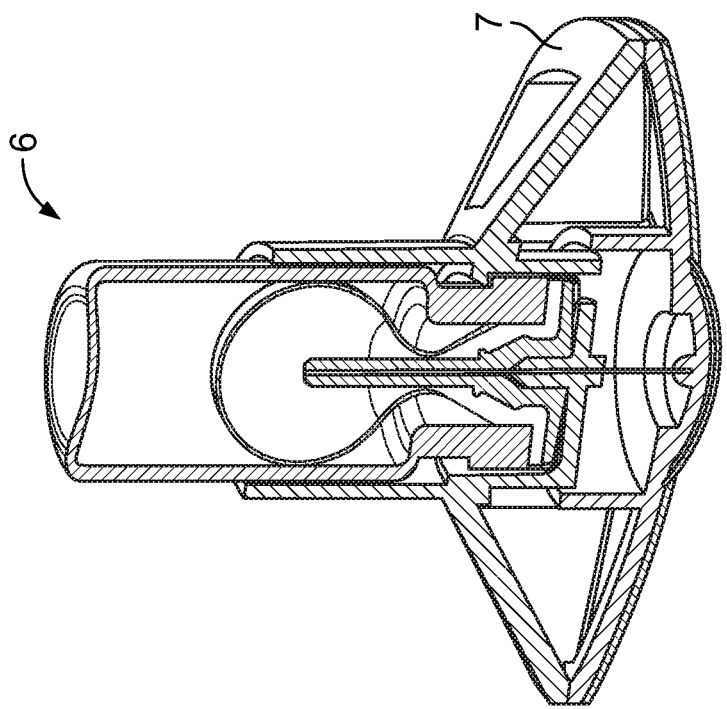

MEDICAL VIAL AND INJECTOR ASSEMBLIES AND METHODS OF USE

RELATED APPLICATIONS

This application is a continuation of U.S. application Ser. No. 14/423,938, filed Feb. 25, 2015, which was the National Stage of International Application No. PCT/US2013/059359, filed Sep. 12, 2013, which claims the benefit of and priority to U.S. Provisional Patent Application Ser. No. 61/704,922, filed Sep. 24, 2012, the contents of each of which are hereby incorporated by reference herein.

FIELD OF DISCLOSURE

This disclosure relates generally to vials for medical liquids, such as drugs, antibiotics, or other liquids for medical therapeutic or diagnostic purposes, and to injection apparatus for injecting the vial contents. More specifically, this subject matter relates to such vials, which can be pre-filled with medical liquid and that can expel substantially all the contents, preferably at a generally constant flow rate, and to injection apparatus or assemblies for use with such vials and to methods of filling and using such vials and apparatus.

The description below is directed to specific exemplary embodiments for the purposes of illustration and not limitation. The features described herein may be employed in other configurations or designs without departing from the scope of this disclosure. PCT International Publication No, WO 2011/123569 A1 is hereby incorporated by reference herein.

BRIEF DESCRIPTION OF DRAWINGS

FIG. 5 is a perspective view of the preferred embodiment of the present invention. In this view the filled vial assembly is being inserted into the injector assembly.

FIG. 6 is cross-sectional view of FIG. 5.

FIGS. 18-22 are cross-sectional views of an alternative embodiment of the injector assembly with vial assembly in place showing different sequences during the injection.

DETAILED DESCRIPTION OF PREFERRED EMBODIMENT

Figure 1:
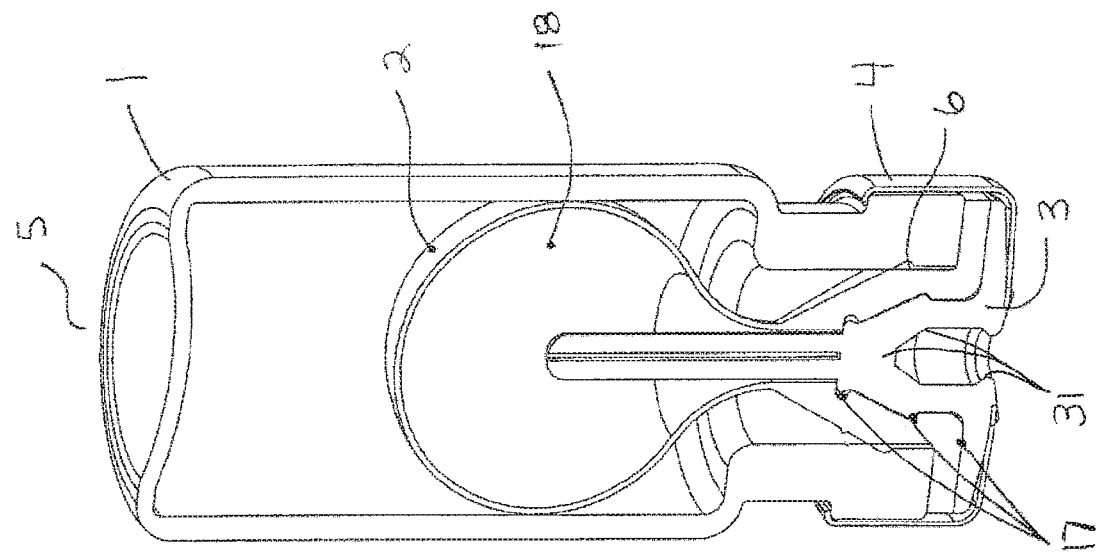
FIG. 1 is a cross-sectional view of a preferred embodiment of the present invention. In this view, the vial assembly is shown in the unfilled state.

Referring to FIG. 1, the vial assembly 5 may include a vial 1, outer stopper/bladder 2, inner plug 3 and crimp cap 4. The vial 1 may be constructed from glass or plastic and range in volume from 1 mL to 10 mL. The crimp cap 4 can be constructed from plastic, aluminum or steel and may include an optional pop-off safety tab. The crimp cap 4 could fit a range of vial neck sizes from 13 to 32 mm in diameter. The outer stopper/bladder 2 (also known as the outer expanding element or balloon) and inner plug 3 can be made from blended synthetic rubber. They may also be independently different materials. This could include one or more of the following in different concentrations: bromobutyl, chlorobutyl, isoprene, polyisoprene, SBR, polybudtadiene, EPDM, natural rubber and silicone. In addition, these rubber components can be coated to improve their surface properties. Coatings may include parylene, silicone, teflon and flourine gas treatments. Alternatively, the outer stopper/bladder 2 and inner plug 3 may be made from a thermoplastic elastomer. The outer stopper/bladder 2 may have irregular wall thickness both in the axial and circumferential direction including ribs or grooves to provide intended variations in stress as a function of strain. This would allow for control over the pressure profile to control the delivery flow rate as a function of diameter extension.

The assembly of the vial 1 may include a sub-assembly of the inner plug 3 and outer stopper/bladder 2 prior to insertion into the vial 1. Alternatively, the outer stopper/bladder 2 can be assembled into the vial 1 and then the inner plug 3 assembled into the outer stopper/bladder 2. Once the outer stopper/bladder 2 and inner plug 3 assembly are placed into the vial 1, the crimp cap 4 is placed onto the vial 1. The crimp force applied by the crimp cap 4 can be varied to achieve different compression forces on the outer stopper/bladder 2 and inner plug 3 assembly. This may allow for control of the seal performance or venting function. The inner plug 3 is configured or sized to provide a pre-stress on the outer stopper/bladder 2 to control the pressure profile as well as to aid in delivery of all or substantially all of the liquid contained within the outer stopper/bladder 2, preferably at about a constant flow rate for most of the injection. A pre-stress between the inner plug 3 and outer stopper/ bladder 2 can be created by making the outer diameter of the inner plug 3 larger than inner diameter of the outer stopper/bladder 2. The inner plug 3 could be a solid piece of material or could be expandable element to control the amount of pre-stress. Gas or liquid could be introduced into a void formed within the inner plug 3 to change its outer diameter or length thus causing varying amounts of pre-stress. Alternatively or additionally, pre-stress can be created by making the inner plug 3 longer than the outer stopper/bladder 2.

Figure 2:
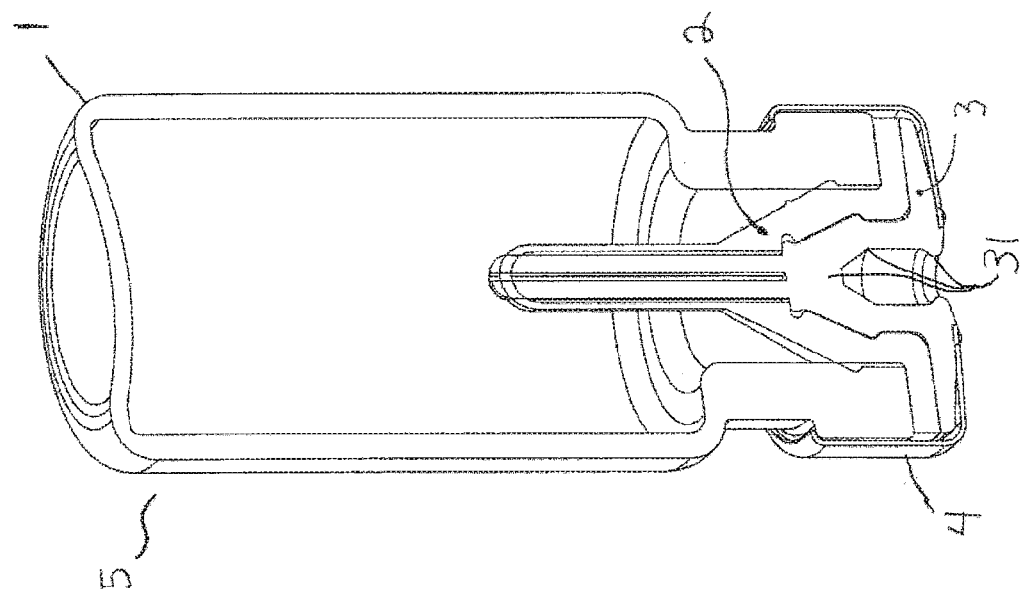
FIG. 2 is a cross-sectional view of a preferred embodiment of the present invention. In this view, the vial assembly is shown in the filled state.

Referring to FIG. 2, liquid 18 is contained within a space formed between the inner plug 3 and outer stopper/bladder 2. The outer stopper/bladder 2 expands like a balloon and applies a uniform pressure on the liquid 18 within this space 2. The shape of the outer stopper/bladder 2 when filled can be spherical or cylindrical. Cylindrical shapes allow for the same stresses as presented in a spherical shape but with more volume. When the vial assembly 5 is coupled with an injector assembly, the pressure exerted by the outer stopper/bladder 2 on the liquid 18 allows for flow of the liquid 18 out of the vial assembly 5 through the needle of the injector assembly into the patient. The outer stopper/bladder 2 is configured with a ring 6 to provide a seal against the inside of the vial 1. The inner plug 3 and outer stopper/bladder 2 are configured to fit together to provide multiple seals between the inner plug 3 and outer stopper/bladder 2. Seals 17 may be configured in a tongue-and-groove or other interlocking system to provide a sealing function. Alternatively or additionally, a seal 17 is provided by the compression of the crimp cap 4 on the inner plug 3 and outer stopper/bladder 2 against the vial 1. Alternatively or additionally, a seal may be formed by the interference between the inner plug 3 and outer stopper/bladder 2.

Figure 3:
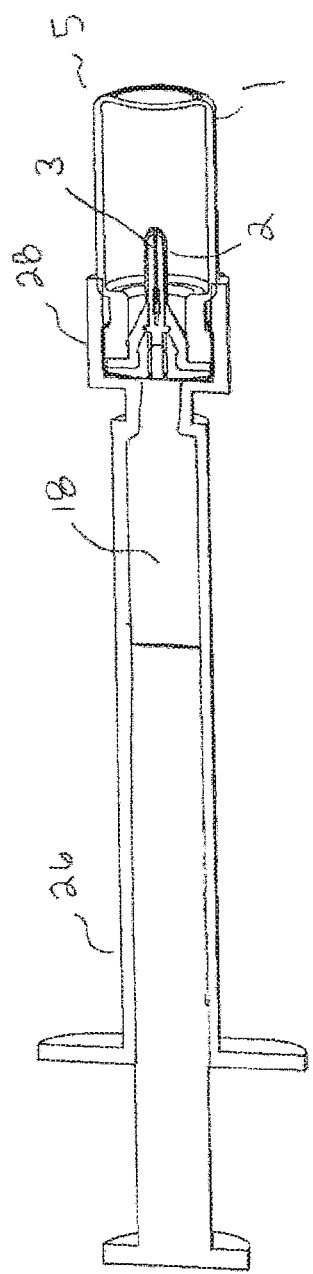
FIGS. 3-4 are cross-sectional views of the vial assembly being filled with a syringe and vial adapter. The vial assembly is shown in the unfilled state in FIG. 3 and shown in the filled state in FIG. 4.
Figure 4:
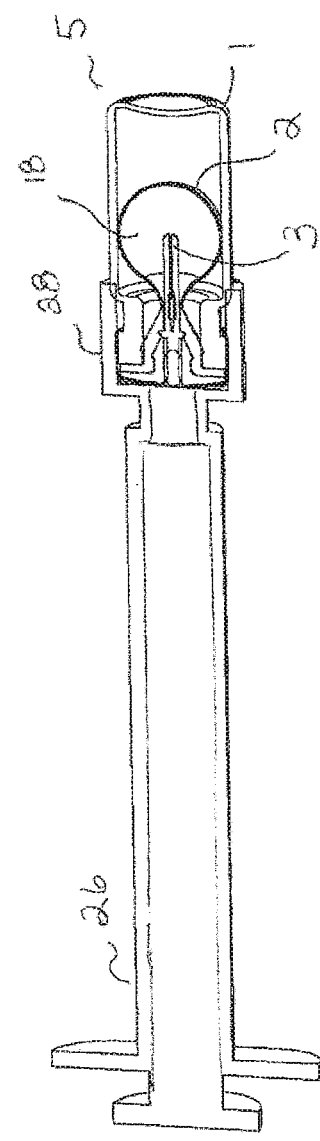

Referring to FIGS. 3 and 4, filling of the vial assembly 5 with liquid 18 can be performed by the user or by filling equipment. A user filled system may include the vial assembly 5 connected to a vial adapter 28 and syringe 26. The syringe 26 and vial adapter 28 is assembled to an empty vial assembly 5. The spike on the vial adapter 28 pierces the solid rubber section of the inner plug 3. The liquid 18 is manually transferred to the vial assembly 5 between the outer stopper/bladder 2 and the inner plug 3 by the user depressing the plunger 27 of the syringe 26 causing the outer stopper/bladder 2 to inflate like a balloon. Once the liquid 18 is transferred to the outer stopper/bladder 2, the syringe 26 and vial adapter 28 are removed. This would be considered filling under liquid pressure. Alternatively, a vacuum could be formed in the space between the outer stopper/bladder 2 and inside of the vial 1 causing the expansion of the outer stopper/bladder 2 to prepare it for receiving liquid. This would be considered filling under no liquid pressure.

Referring to FIGS. 5 and 6, the injector assembly 6 for injecting the contents of the vial assembly 5 described earlier preferably, but not exclusively, includes a vial holder 7, needle hub 8, needle 25, adhesive 9, outer housing 10, safety pin 11, double-sided tape 12, bandage 13 and outer bandage cover 14. Additionally, the injector assembly 6 could have the vent needle 15. The vial holder 7 allows for containment of the vial assembly 5 and interfaces with the needle hub 8, outer housing 10 and safety pin 11. There are cutouts 19 in the side of the vial holder 7 to allow for viewing of the vial assembly 5. Alternatively, the vial holder 7 may have transparent viewing windows. This allows for viewing the vial assembly 5 to confirm the proper dose has been delivered. The needle hub 8 allows for containment of the needle 25 and interfaces with the vial holder 7, adhesive 9 and inner plug 3. The needle hub 8 can move relative the vial holder 7 and inner plug 3 and allows for communication of the needle 25 with the liquid 18 in the outer stopper/bladder 2 during dispense. The needle hub 8 may also have the ability for rotational movement to dislocate the needle 25 during removal of the injector assembly 6 for needle stick safety. The needle 25 interfaces with the adhesive 9, needle hub 8, bandage 13 and inner plug 3. The needle 25 pierces the solid rubber portion of the inner plug 3 to allow for communication of the liquid 18 contained within the outer stopper/bladder 2 during dispense. The needle 25 pierces the bandage 13 during activation of the injector assembly 6 prior to dispense of the liquid. The needle 25 inner diameter and length combined with the performance characteristics of the vial assembly 5 allow for control of the flow rate of the liquid during dispense. The adhesive 9 is used to bond the needle 25 to the needle hub 8. This adhesive 9 could be for example, epoxy or cyanoacrylate and be air, moisture or UV cured.

The outer housing 10 interfaces with the vial holder 7, needle hub 8, safety pin 11 and double-sided tape 12. It provides the means to locate the injector assembly 6 onto the skin surface. The safety pin 11 prevents inadvertent advancement of the vial holder 7 relative to the outer housing 10 prior to intended use of the injector assembly 6. The safety pin 11 interfaces with the outer housing 10 and vial holder 7. The safety pin 11 can be configured to allow for radial and rotational movement relative to the outer housing 10. The double-sided tape 12 allows for attachment of the outer housing 10 to the skin surface. It also holds the bandage 13 to the outer housing 10 until the outer housing 10 is removed from the skin surface. The bandage 13 allows for wound protection after the injector assembly 6 is removed from the skin surface. The bandage 13 interfaces with the outer housing 10, double-sided tape 12 and the outer bandage cover 14. The adhesion force between the bandage 13 and the skin surface is greater than the adhesion force between the bandage 13 and the double-sided tape 12. This allows for removal of the injector assembly 6 from the skin surface without removal of the bandage 13. The double-sided tape 12 interfaces with the outer housing 10, bandage 13 and outer bandage cover 14. The outer bandage cover 14 provides for protection of the bandage 13 and double-sided tape 12 prior to use of the injector assembly 6. The outer bandage cover 14 is removed prior to use of the injector assembly 6 and interfaces with the double-sided tape 12 and bandage 13.

Figure 9:
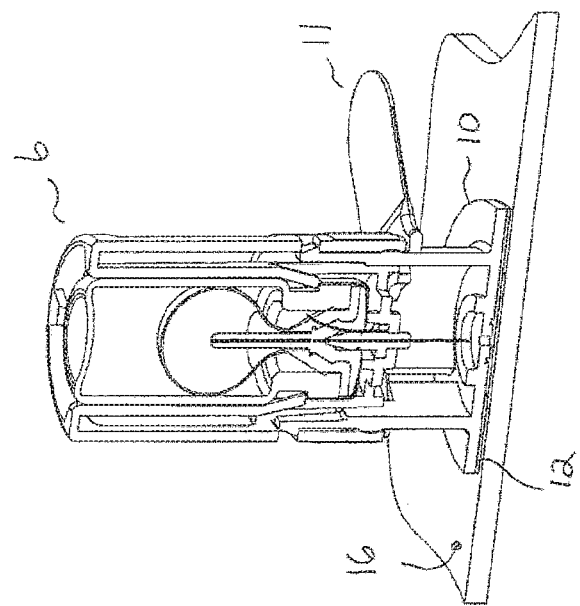
FIGS. 7-14 are cross-sectional views of the preferred embodiment of the present invention of the injector assembly with vial assembly in place showing different sequences during the injection.
Figure 8:
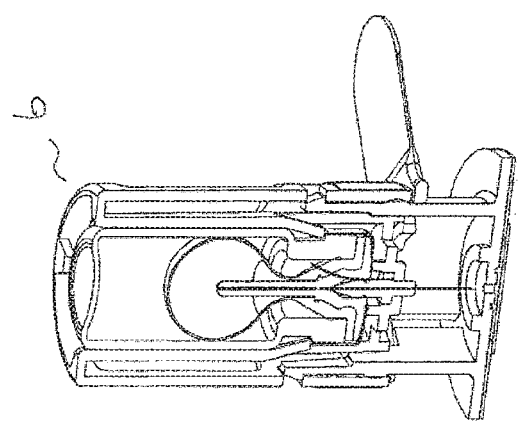
Figure 7:
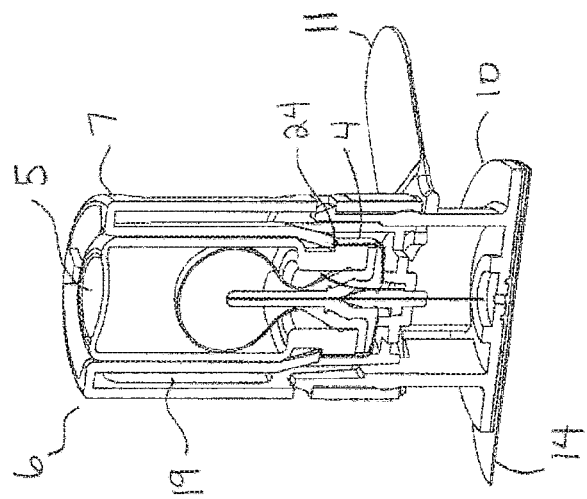

Referring to FIGS. 7-9, the vial assembly 5 is inserted into the injector assembly 6 until snaps 24 in the vial holder 7 interface with the crimp cap 4 on the vial assembly 5 to prevent it from being removed. The top of the vial assembly 5 may be flush with the top of the vial holder 7 allowing for one method of verification that the vial assembly 5 is sufficiently inserted into the injector assembly 6. The vial holder 7 or vial assembly 5 cannot advance relative to the outer housing 10 as the safety pin 11 keeps them from advancing. Cutouts 19 in the vial holder 7 allow the user to view the inside of the vial assembly 5. In FIG. 8, the outer bandage cover 14 is removed from the bottom of the injector assembly 6. It is ready to be attached to the skin surface 16. In FIG. 9, the injector assembly 6 can be attached to the skin surface 16. The double-sided tape 12 will provide the adhesion force between the outer housing 10 and the skin surface 16.

Figure 12:
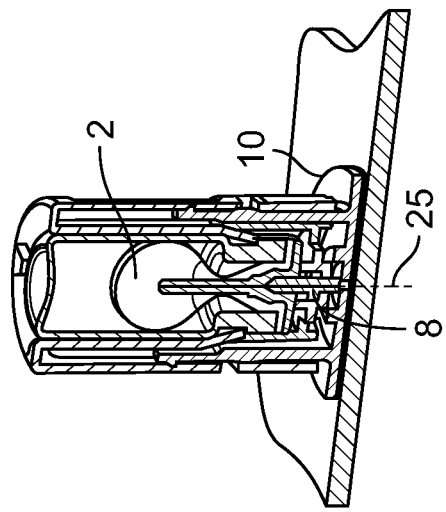
Figure 11:
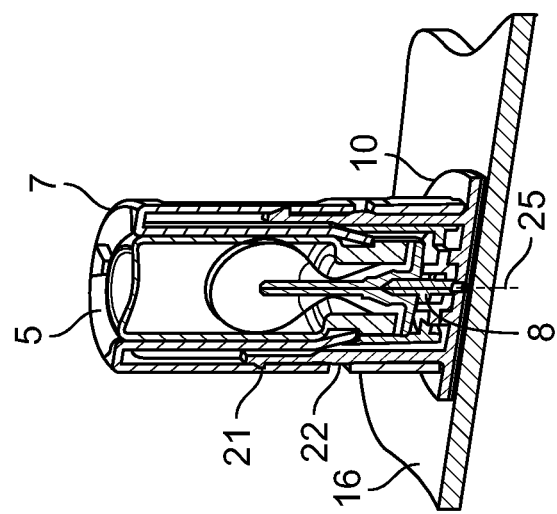
Figure 10:
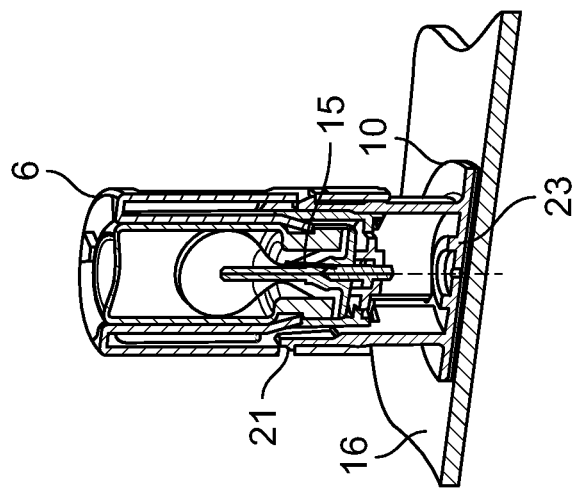

Referring to FIGS. 10-12, once the injector assembly 6 is place on the skin surface 16, the safety pin 11 is removed from the injector assembly 6 and it is ready for actuation. Detent features 21 in the vial holder 7 and outer housing 10 prevent the vial holder 7 from moving relative to the outer housing 10 without user intervention. In FIG. 11, the user pushes down on the vial holder 7 to begin inserting the needle 25 into the skin surface 16. Ramp features (over-center mechanism) 22 in the vial holder 7 and outer housing 10 allow for relatively small applied force by the user to produce a relatively large axial movement of the vial holder 7 into the outer housing 10. Axial movement of the vial holder 7, vial assembly 5, needle hub 8 and needle 25 (in unison) continues until the needle hub 8 bottoms out on the outer housing 10. In FIG. 12, the needle 25 and needle hub 8 motion stop relative to the outer housing 10 just before the needle 25 is in communication with the fluid in the outer stopper/bladder 2. While a latch/lockout 23 releases the vial holder 7 for an additional small movement to allow the needle 25 to pierce the solid section of the inner plug 3 and allowing communication of the needle 25 with the liquid in the outer stopper/bladder 2. The latch/lockout 23 allows for complete needle 25 travel into the skin surface 16 before the start of dispense. The needle 25 enters the liquid space within a cutout 19 in the inner plug 3. This small amount of motion also allows the vent needle 15 to pierce the wall of the outer stopper/bladder 2 to allow for venting of the space between the outer stopper/bladder 2 and the inside of the vial 1.

Figure 15:
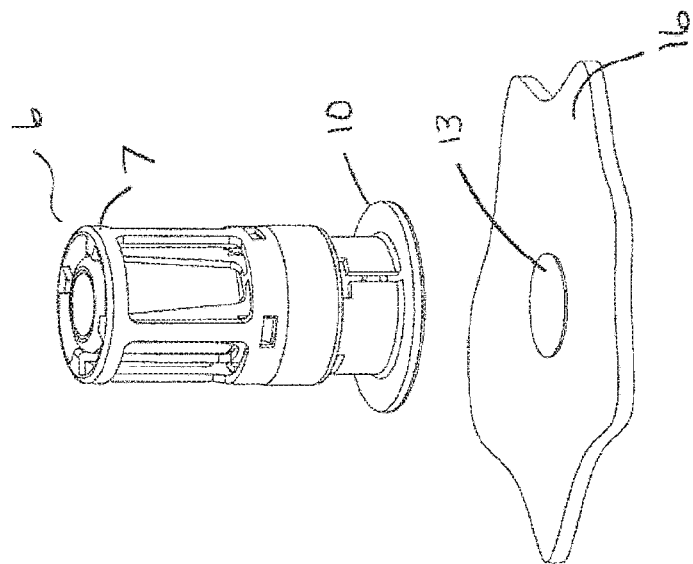
FIG. 15 is a perspective view of the preferred embodiment of the present invention of the injector assembly being removed from the injection surface after delivery of the liquid.
Figure 14:
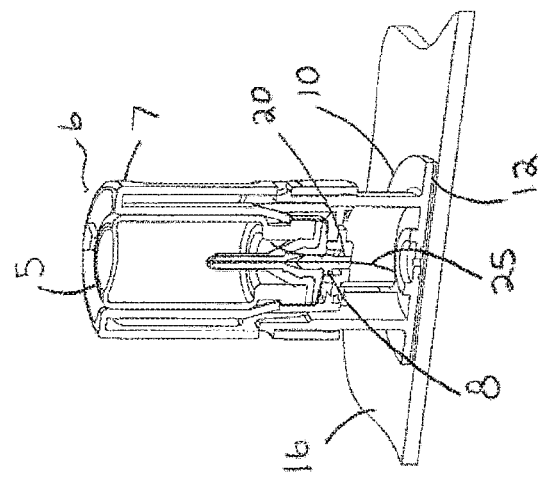
Figure 13:
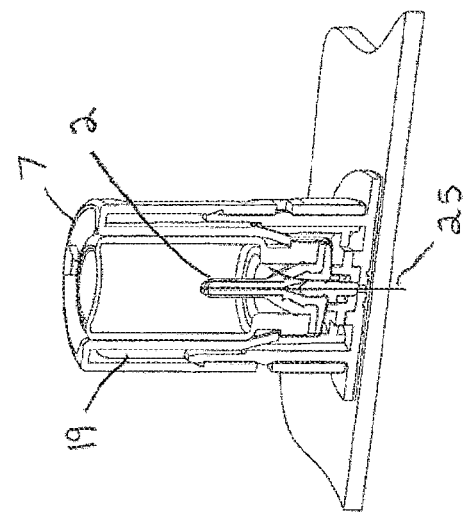

Referring to FIGS. 13-15, once the needle 25 is in communication with the liquid, substantially all of the liquid (preferably more than 95% and more preferably 99%) within the outer stopper/bladder 2 is dispensed into the user. Cutouts 19 in the vial holder 7 allow the user to visually confirm the entire amount of liquid was dispensed. In FIG. 14, the dispense is completed and the user begins to remove the injector assembly 6 by pulling up on the vial holder 7. The adhesion force between the double-sided tape 12 and the skin surface 16 holds the outer housing 10 to the skin surface 16. Axial movement of the vial holder 7, vial assembly 5, needle hub 8 and needle 25 (in unison) continues relative to the outer housing 10 until the needle 25 is completely retracted into the outer housing 10, shielding it from the user. Once inside the outer housing 10, the needle 25 may be deflected to a stored position that prevents reuse and protects against accidental needle stick by the user. For example, snaps 20 in the outer housing 10 interface with the needle 25 and needle hub 8 to move it off center, slightly bending it and locking it out from being actuated again while also providing for additional needle shielding from the user. At the end of the vial holder 7 travel within the outer housing 10, the injector assembly 6 is pulled away from the skin surface 16. The bandage 13 peels away from the outer housing 10 and is left behind on the skin surface 16.

DETAILED DESCRIPTION OF ALTERNATIVE EMBODIMENTS

Figure 17:
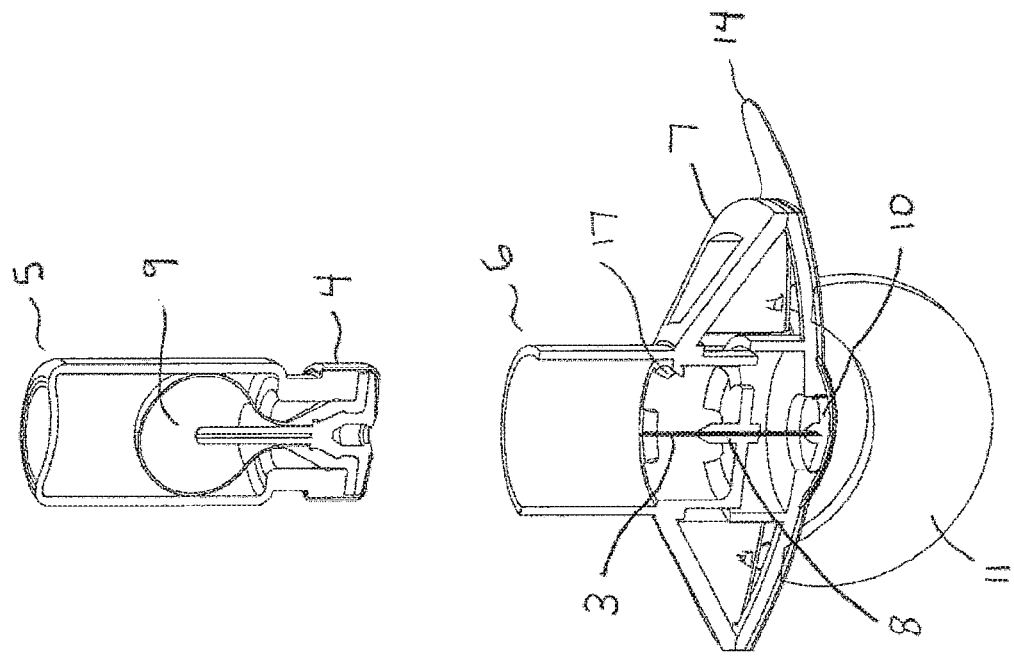
FIG. 17 is cross-sectional view of FIG. 16.
Figure 16:
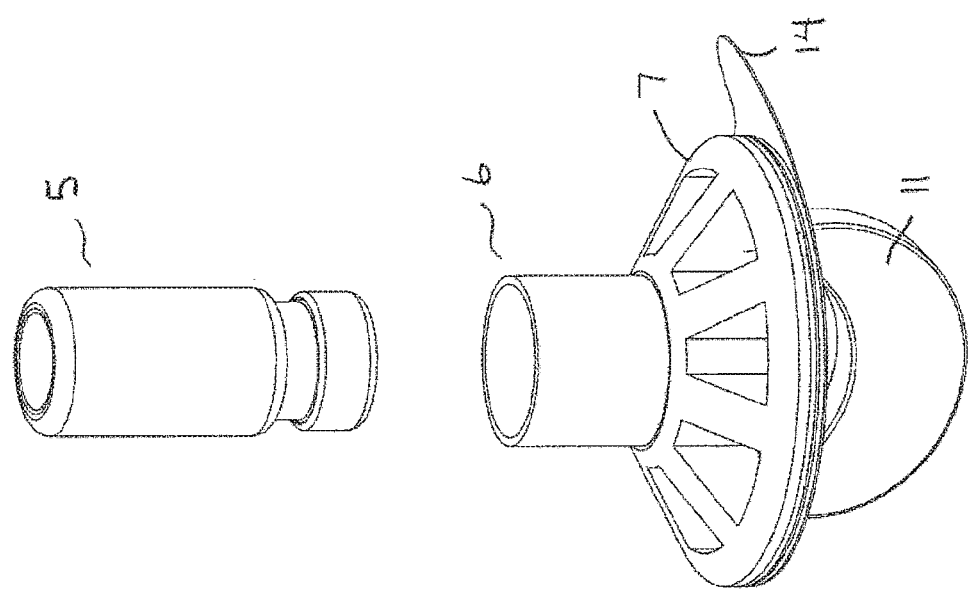
FIG. 16 is a perspective view of an alternative embodiment. In this view the filled vial assembly is being inserted into the injector assembly.

Referring to FIGS. 16-17, in this embodiment, the vial holder and outer housing are preferably one piece, with an upper vial holder and lower base for contacting the skin of the patient. These upper and lower housing portions are hinged along an annular junction along the outer perimeter of the outer housing. The needle hub 8 can be separate or configured as part of the vial holder/outer housing 17. The vial assembly 5 is inserted into the injector assembly 6 until snaps 17 in the vial holder/outer housing 7 interface with the crimp cap 4 on the vial assembly 5 to prevent it from being removed. In this embodiment, the vial access end of the needle 3 is in communication with the liquid (drug, antibiotic or other medicament) 18 when the vial assembly 5 is inserted into the injector assembly 6. The injection end of the needle 3 is embedded in an elastomeric needle shield 10 which prevents liquid 9 from coming out of the needle 3. The vial assembly 5 cannot advance relative to the vial holder/outer housing 7 as the safety pin 11 keeps them from advancing. The injector assembly 6 is also covered with an outer bandage cover 14.

Referring to FIGS. 18-19, the outer bandage cover 14 and safety pin 11 is removed from the injector assembly 6 and it is ready for actuation. In FIG. 19, the injector assembly 6 can be attached to the skin surface 16. The double-sided tape 12 will provide the adhesion force between the contact surface 15 of the vial holder/outer housing 7 and the skin surface 16. As illustrated in FIG. 19, the skin-facing surface of the housing includes a skin-facing protrusion 41.

Figure 21:
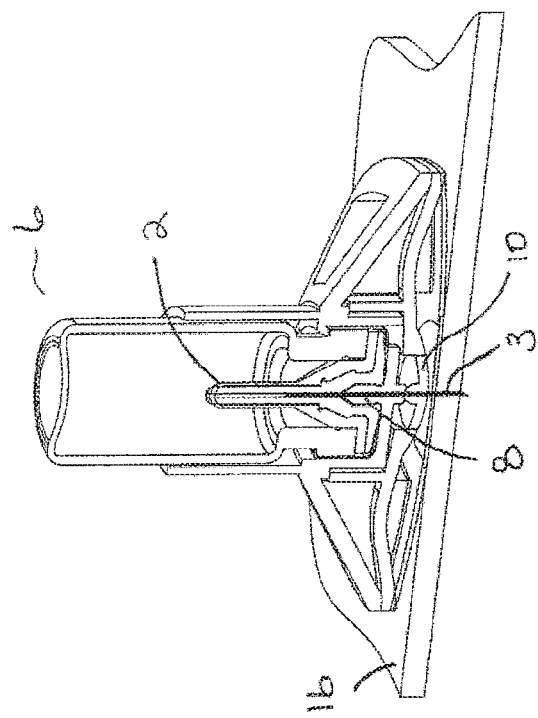
Figure 20:
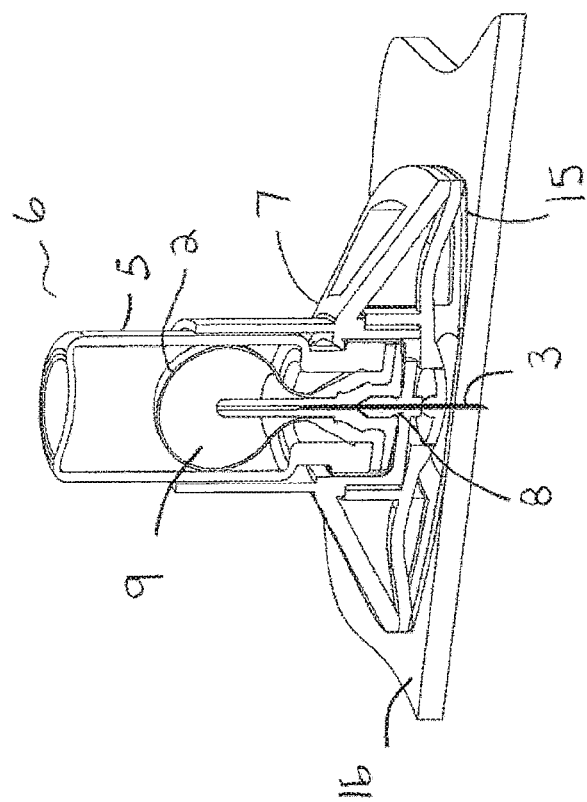

Referring to FIGS. 20-21, when the user attaches the injector assembly 6 to the skin surface 16, the contact surface 15 of vial holder/outer housing 7 is designed to flex into the injector assembly 6, providing for an over-center action to produce a relatively large axial movement of the contact surface 15 into the holder/outer housing 7. Axial movement of the contact surface 15 of vial holder/outer housing 7 relative to the vial assembly 5, needle hub 8 and needle 3 continues until the needle hub 8 bottoms out on the vial holder/outer housing 7. Additionally, the needle 3 passes through the needle shield 10 allowing for flow of the liquid 9 out of the needle 3 into the skin surface 16. Additionally, this axial movement allows for complete needle travel into the skin surface 16. In FIG. 21 substantially all of the liquid 9 (preferably more than 95% and more preferably 99%) within the outer stopper/bladder 2 is dispensed into the user.

Figure 23:
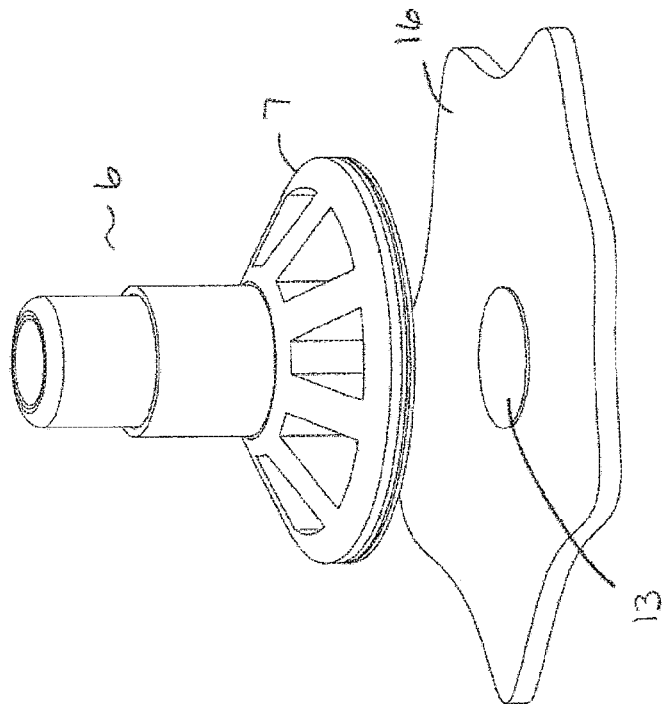
FIG. 23 is a perspective view of an alternative embodiment of the injector assembly being removed from the injection surface after delivery of the liquid.
Figure 22:
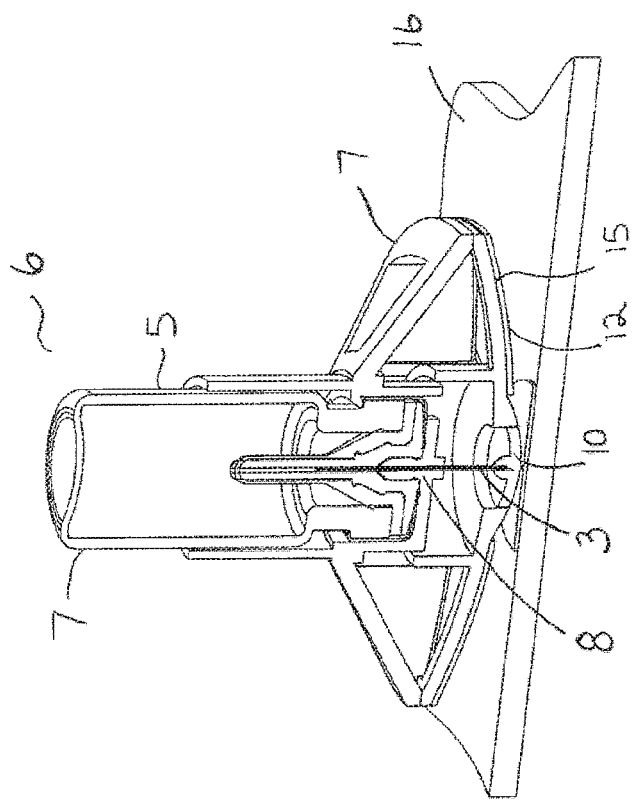

Referring to FIGS. 22-23, the dispense is completed and the user begins to remove the injector assembly 6 by pulling up on the vial holder/outer housing 7. The adhesion force between the double-sided tape 12 attached to the contact surface 15 of the vial holder/outer housing 7 and the skin surface 16 causes the contact surface 15 to flex back to its original starting position. This provides for an over-center action to produce a relatively large axial movement of the contact surface 15 out of the vial holder/outer housing 7. Axial movement of the contact surface 15 allows for axial movement of the vial holder/outer housing 7, vial assembly 5, needle hub 8 and needle 3 until the needle 3 is completely retracted into the vial holder/outer housing 7, embedding the needle 3 back into the needle shield 10, shielding it from the user. When the injector assembly 6 is pulled away from the skin surface 16, the bandage 13 peels away from the vial holder/outer housing 7 and is left behind on the skin surface 16.

Figure 25:
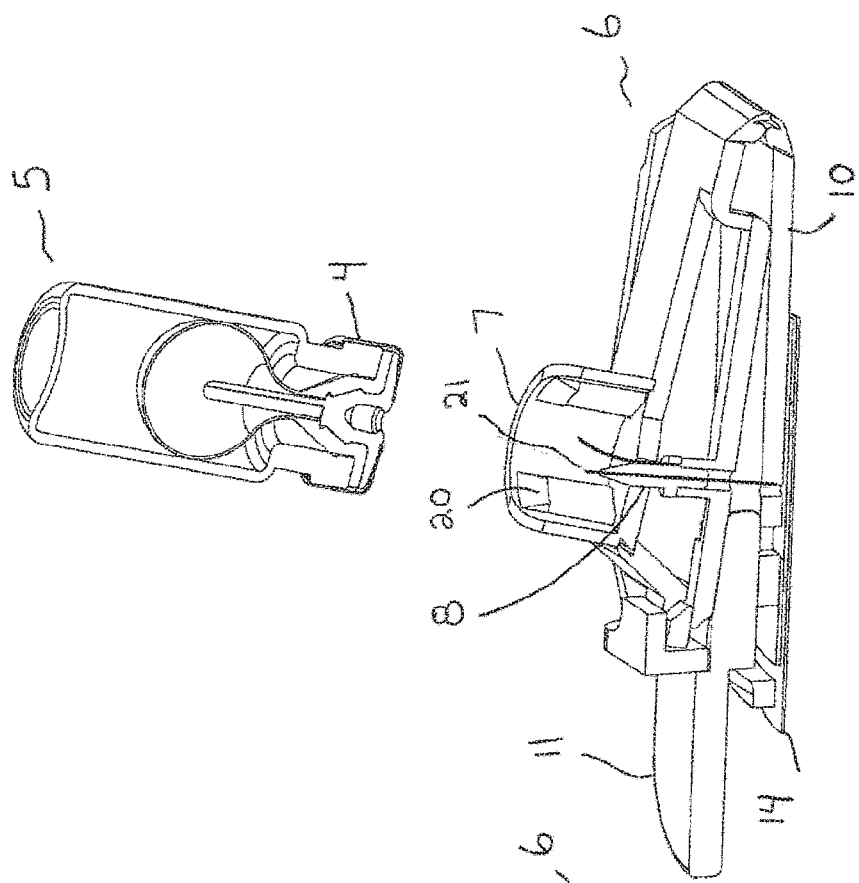
FIG. 25 is cross-sectional view of FIG. 24.
Figure 24:
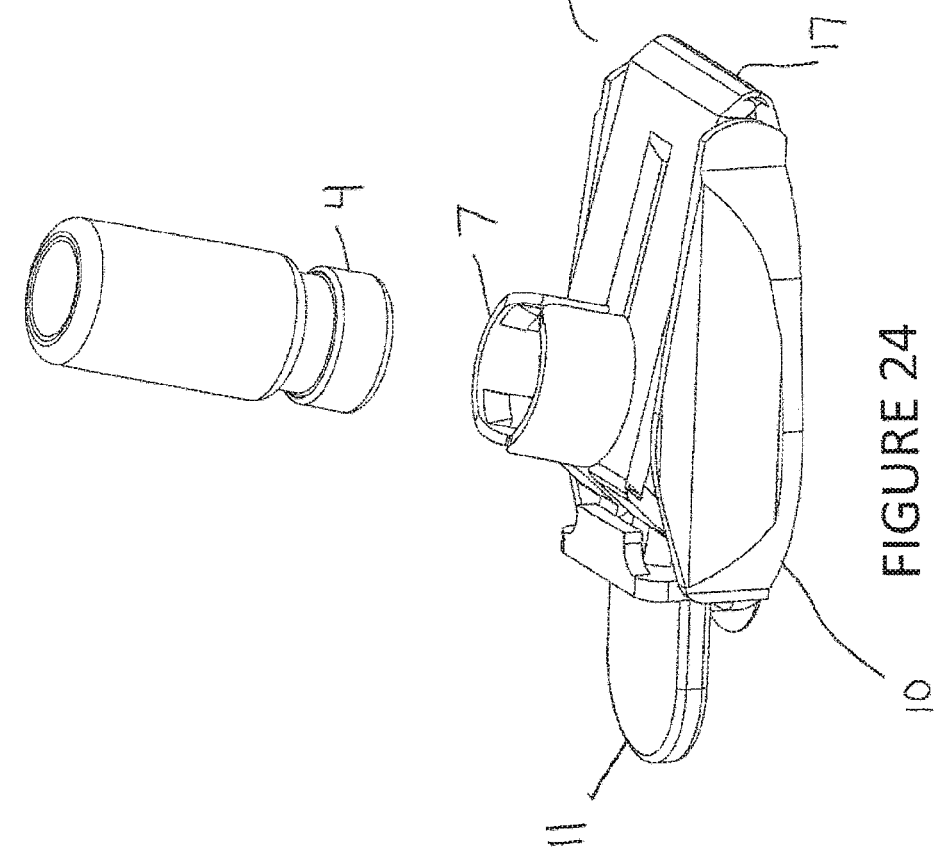
FIG. 24 is a perspective view of an alternative embodiment of an injector assembly. In this view the filled vial assembly is being inserted into the injector assembly.

Referring to FIGS. 24-25, in this embodiment, the vial holder 7 and the outer housing 10 are joined by a flexible hinge 17. The injector assembly 6, as seen in FIG. 25, has three relatively moveable that can pivot relative to one another including a vial holder 7, a needle hub 8, needle 21 and the outer housing 10. The vial assembly 5 is inserted into the injector assembly 6 until snaps 20 in the vial holder 7 interface with the crimp cap 4 on the vial assembly 5 to prevent it from being removed. The vial holder 7 cannot advance relative to the outer housing 10 as the safety pin 11 keeps it from advancing. The bottom of the outer housing 10 is covered with an outer bandage cover 14.

Figure 27:
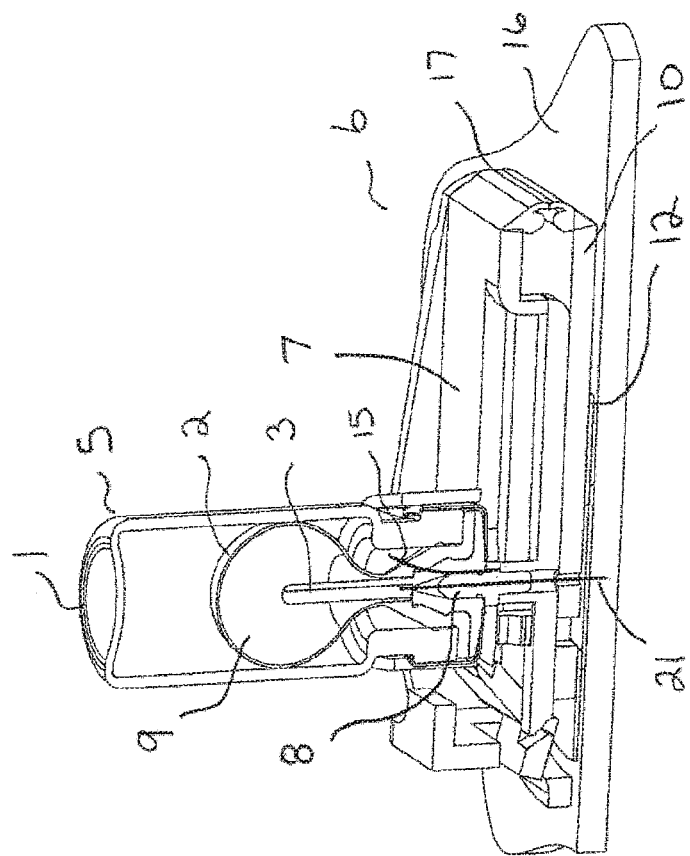
FIGS. 26-29 are cross-sectional views of an alternative embodiment of the injector assembly with vial assembly in place showing different sequences during the injection.
Figure 26:
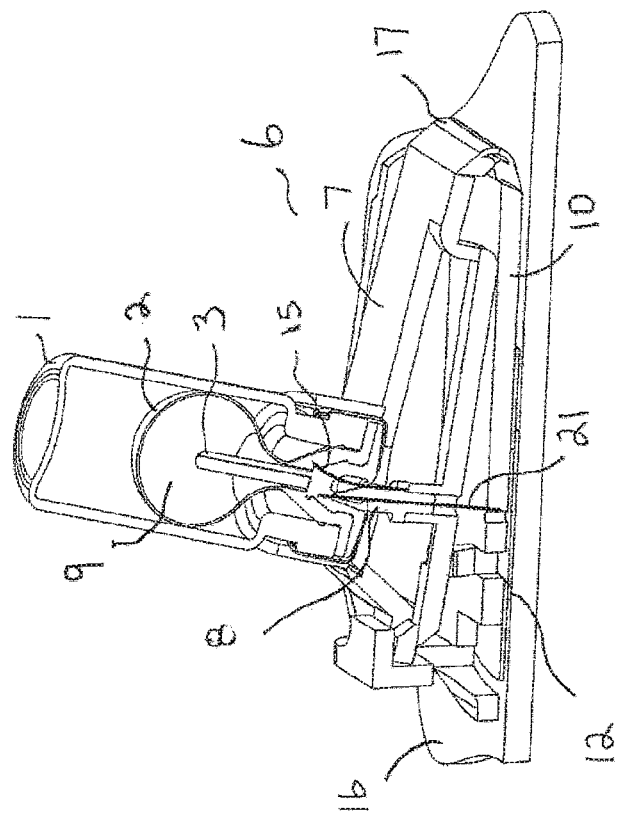

Referring to FIGS. 26-27, the outer bandage cover 14 is removed from the bottom or base of the injector assembly 6. It is ready to be attached to the skin surface 16. The double-sided tape 12 will provide the adhesion force between the outer housing 10 and the skin surface 16. Once the injector assembly 6 is placed on the skin surface 16, the safety pin 11 is removed from the injector assembly 6 and it is ready for actuation. In FIG. 26, the user pushes down on the vial holder 7 to begin inserting the needle 21 into the skin surface 16. Slight rotational movement of the vial holder 7, vial assembly 5, needle hub 8 and needle 21 (in unison) about the flexible hinge 17 continues until the needle hub 8 bottoms out on the outer housing 10. In FIG. 27, the needle 21 and needle hub 8 motion stop relative to the outer housing 10 just before the needle 21 is in communication with the fluid in the outer stopper/bladder 2. An additional small movement allows the needle 21 to pierce the solid section of the inner plug 3 allowing communication of the needle 21 with the liquid 9 in the outer stopper/bladder 2. This allows for complete needle 21 travel into the skin surface 16 before the start of dispense. The needle 21 enters the liquid space within a cutout 19 in the inner plug 3. This small amount of motion also allows the vent needle 15 to pierce the wall of the outer stopper/bladder 2 to allow for venting of the space between the outer stopper/bladder 2 and the inside of the vial 1.

Figure 29:
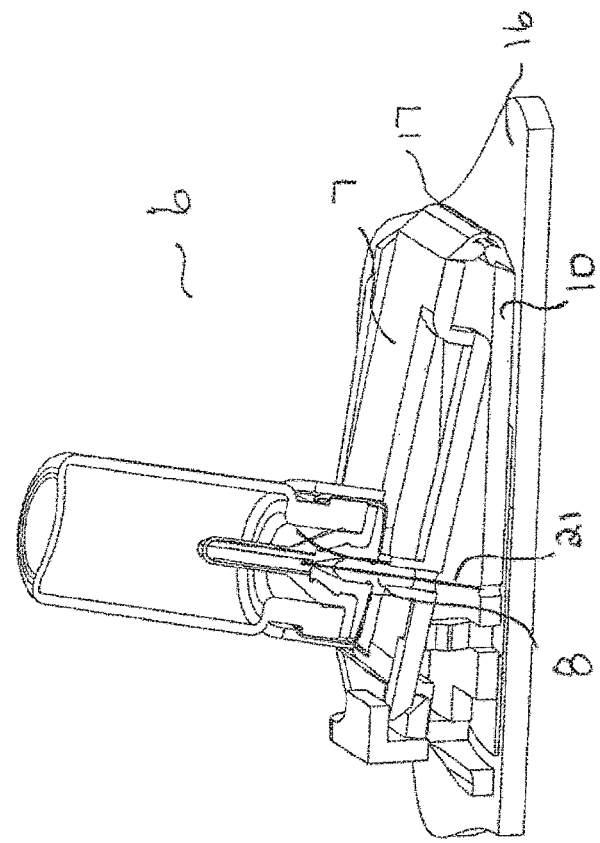
Figure 28:
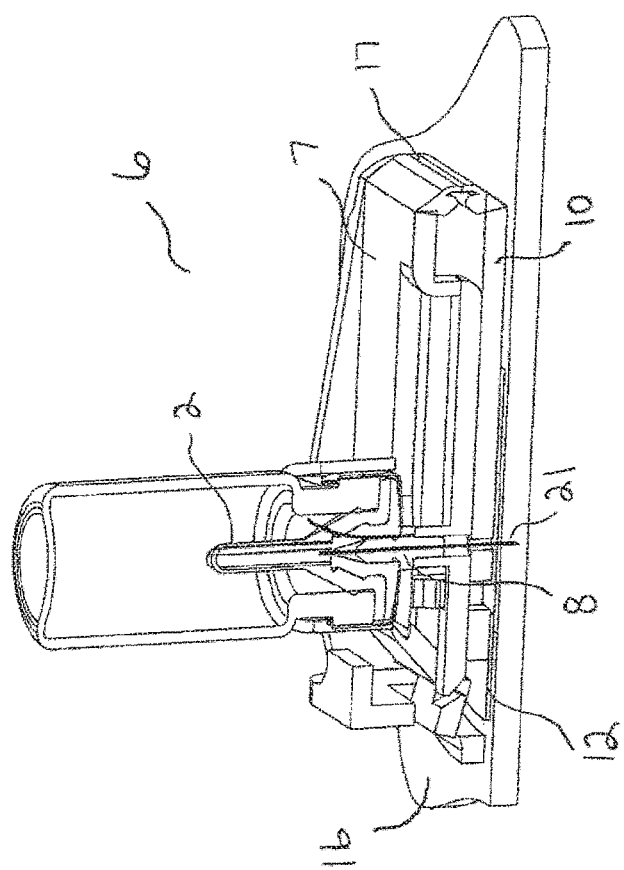

Referring to FIGS. 28-29, once the needle 21 is in communication with the liquid, substantially all of the liquid (preferably more than 95% and more preferably 99%) within the outer stopper/bladder 2 is dispensed into the user. In FIG. 29, the dispense is completed and the user begins to remove the injector assembly 6 by pulling up on the vial holder 7. The adhesion force between the double-sided tape 12 and the skin surface 16 holds the outer housing 10 to the skin surface 16. Rotational movement about the flexible hinge 17 of the vial holder 7, vial assembly 5, needle hub 8 and needle 21 (in unison) continues relative to the outer housing 10 until the needle 21 is completely retracted into the outer housing 10, shielding it from the user.

Figure 30:
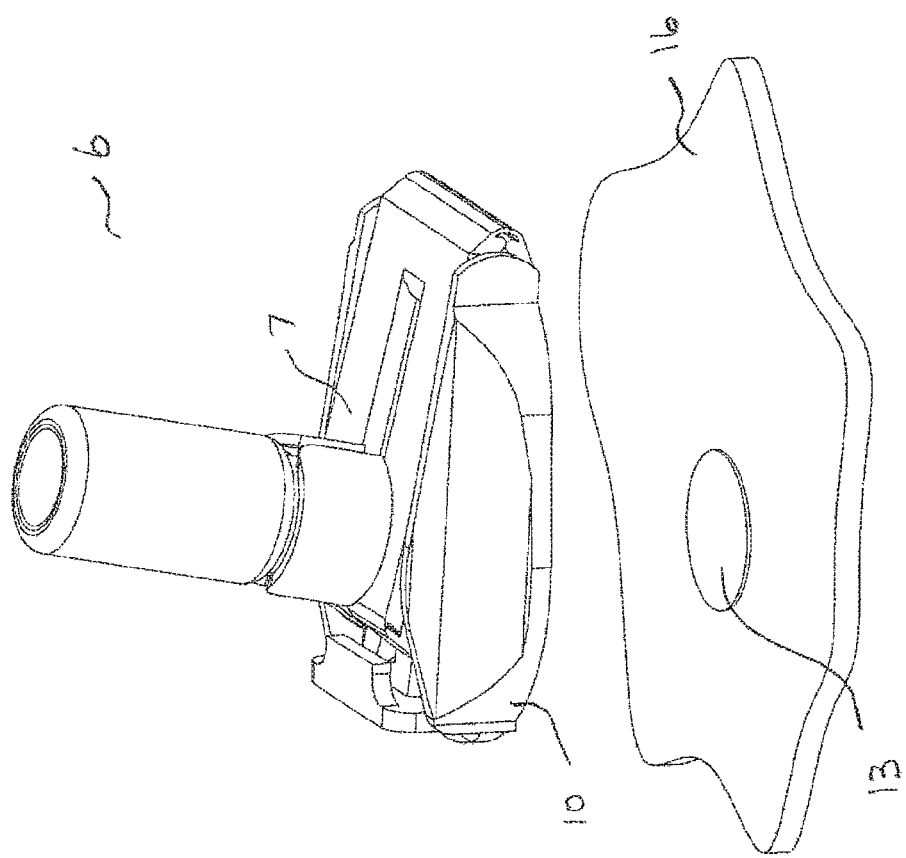
FIG. 30 is a perspective view of an alternative embodiment of the injector assembly being removed from the injection surface (e.g. patient's skin) after delivery of the liquid.

Referring to FIG. 30, at the end of the vial holder 7 travel relative the outer housing 10, the injector assembly 6 is pulled away from the skin surface 16. The bandage 13 peels away from the outer housing 10 and is left behind on the skin surface 16.

FURTHER DESCRIPTION OF PREFERRED EMBODIMENT

Figure 32:
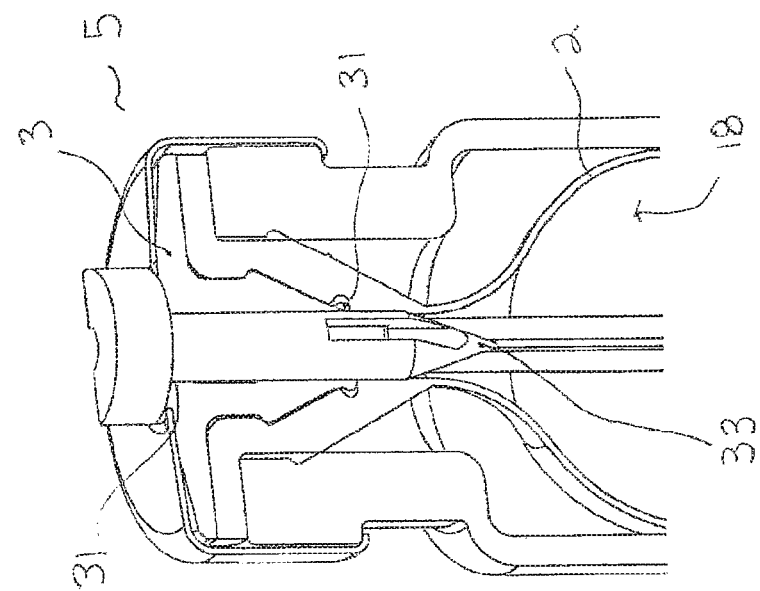
FIG. 32 is a cross-sectional perspective view of the vial of FIG. 31 with filling apparatus fully inserted.
Figure 31:
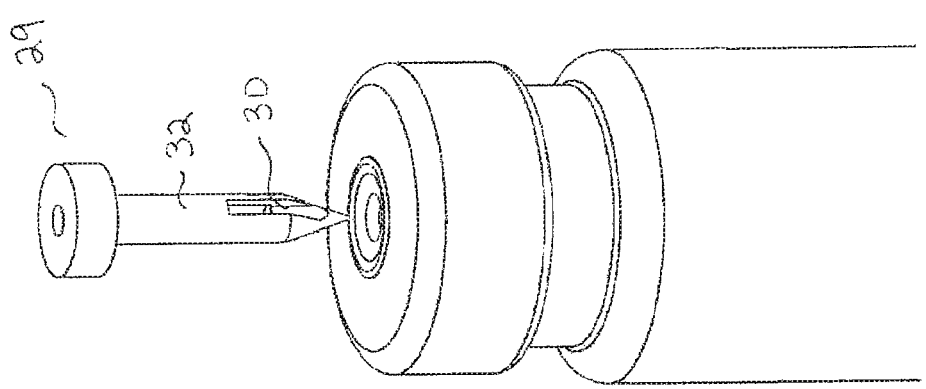
FIG. 31 is a perspective view of a vial such as in FIG. 1 and a filling apparatus or spike for introducing medical liquid into the vial.

Referring to FIGS. 31-32, a filling apparatus 29 such as a filling needle, vial adapter spike or other means of filling may be used to introduce liquid 18 into the outer stopper/bladder 2 of the vial assembly 5. A filling apparatus 29 may have one or more slots 30 integral to its body 32, and communicating with an internal fill path that extends to a fill inlet that may be a luer port or other inlet. To allow for filling of the outer stopper/bladder 2 of the vial assembly 5 using a filling apparatus 29, one and preferably two or more inner seals 31 may be configured into the inner stopper or plug 3 to interface with the body or shaft 32 of the filling apparatus 29 during filling and subsequent removal of the body 32 of the filling apparatus 29. Alternatively or additionally, multiple inner seals 31 may be configured with an axial spacing to cover the slot 30 of the body 32 of the filling apparatus 29 to prevent loss of internal pressure or liquid 18 within the outer stopper/bladder 2 during the filling process. Alternatively or additionally, multiple inner seals 31 may be configured with an axial spacing to prevent communication between the internal space of the outer stopper/bladder 2 and the ambient environment resulting in loss of pressure or liquid 18 through the slot 30 of the body 32 of the filling apparatus 29 during retraction after filling. In FIG. 32, the tip 33 of the filling apparatus 29 is shown fully inserted into the inner plug 3. The filling apparatus 29 is in communication with the outer stopper/bladder 2 and the inner seals 31 prevent loss of internal pressure or liquid 18 within the outer stopper/bladder 2 for sealing the pressure in the bladder as the fill apparatus or spike is retracted out of the filled pressurized bladder volume while maintaining a seal between the spike and ambient pressure. Specifically, the distance or zone between two inner seals is greater than the length of slots 30, whereby the fill apparatus or spike is sealed at least one location, such as proximal to the slots or distal to the slots, as the spike is inserted or retracted.

Figure 34:
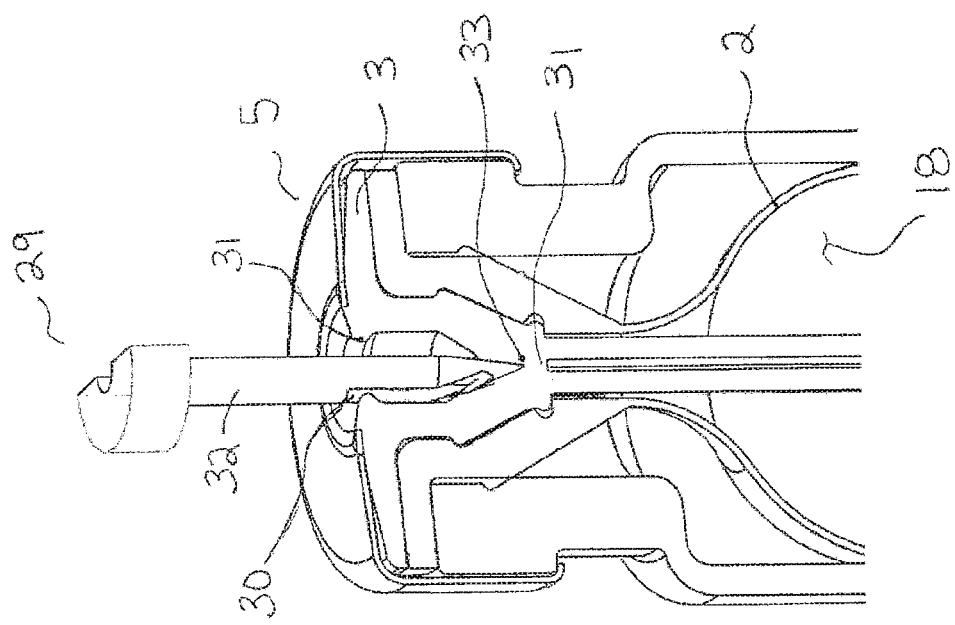
FIG. 34 is a cross-sectional perspective view of the vial of FIG. 33, with the filling apparatus further withdrawn or less inserted.
Figure 33:
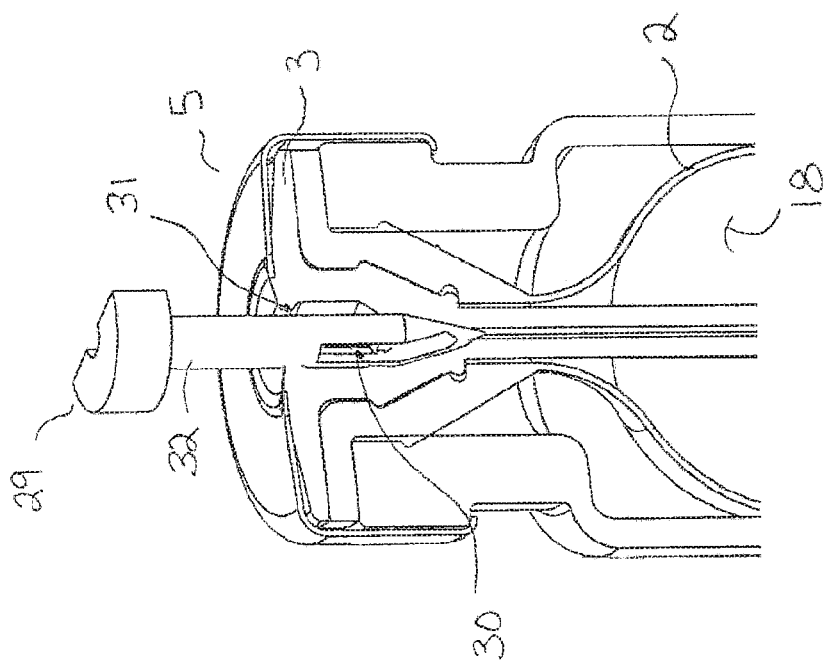
FIG. 33 is a cross-sectional perspective view of the vial of FIG. 32, with the filling apparatus partially withdrawn or partially inserted.

Referring to FIGS. 33-34, the filling apparatus 29 is partially withdrawn from the inner plug 3 of the vial assembly 5. The filling apparatus 29 is in communication with the outer stopper/bladder 2. The top of the slot 30 of the body 32 of the filling apparatus 29 is covered by the upper inner seal 31 to prevent loss of internal pressure or liquid 18 within the outer stopper/bladder 2 during withdraw of the filling apparatus. In FIG. 34, the filling apparatus 29 is further withdrawn from the inner plug 3 of the vial assembly 5. The top of the slot 30 of the body 32 of the filling apparatus 29 is exposed to the ambient environment but the tip 33 of the filling apparatus 29 is sealed by the lower inner seal 31. This prevents communication between the filling apparatus 29 and outer stopper/bladder 2 and thus prevents loss of internal pressure or liquid 18 within the outer stopper/bladder 2 during withdrawal of the filling apparatus 29.

The foregoing description contains numerous independent concepts, features and functions that have utility and may be claimed separately and in combination with other concepts, features or functions, including, without limitation:

(1) a vial with resilient inner bladder for containing a drug, antibiotic or other medical liquid injectable and a pre-stress member within the bladder;

(2) a method of making, filling and using such a vial;

(3) a vial injection assembly for injecting the contents of such a pre-filled vial into a patient;

(4) the combination of such a vial injection assembly and pre-filled vial;

and (5) a method of injecting the contents of a pre-filled vial through the skin of a patient;

(6) a vial subassembly comprising a resilient bladder and a pre-stress member within the bladder; and (7) a slotted fill apparatus or spike in combination with plural internal vial seals that define a seal zone between the seals longer than the spike slots(s) to seal the bladder during insertion and withdrawal of the spike.

The foregoing concepts are useful and may be claimed alone or with one or more of the other above concepts and/or with other features or functions described herein, including, without limitation, features and/or functions that:

(A) provide for injection of substantially all the vial contents, preferably at least 95% and more preferably at least 99%;

(B) provide for injection of most of the vial contents at substantially constant flow rates;

(C) provide for sequential steps or stages in the injection assembly for advancing a vial from a loading configuration to an injection configuration;

(D) protect an injection needle against inadvertent needle sticks;

(E) prevent reuse of the injection assembly;

(F) automatically provide a bandage at the site of the injection;

(G) provide an injection without substantial user discomfort;

(H) vent displacement air into a vial between a pre-filled bladder and vial housing during injection;

(I) retain the injection assembly on the skin of a patient until removed by the user;

(J) permit filling of an internal vial bladder either manually or by large scale filling equipment;

(K) allow pre-stress of the vial bladder to be changed by changing the size or configuration of a pre-stress member located within the bladder; and/or (L) provide any combination of the above concepts and/or features or functions.

What is claimed is:

1. A medical fluid injection device that may be adhered to the skin of a patient, the device including:
   a housing including a skin-facing surface;
   a medical fluid reservoir defined by an expandable elastomeric bladder that is expandable upon the pressurized introduction of medical fluid thereinto, the elastomeric bladder when so expanded exerting a force on the medical fluid therewithin and the elastomeric bladder including a bladder first end and a bladder second end;
   a pre-stress member disposed at least in part within the bladder, the pre-stress member having a member first end and a member second end and a size larger than the size of the bladder in a non-pressurized condition, wherein the bladder first end and the member first end are secured together and the bladder second end and the member second end are detached so that the bladder second end is configured to move away from the member second end upon the pressurized introduction of medical fluid into the bladder; and
   an injection needle including an injection end movable between a retracted position within the housing and an injection position extending through the skin facing surface of the housing for injection into a patient, the needle being in fluid communication with the bladder in the injection position.

2. The medical fluid injection device of claim 1 in which the bladder and pre-stress member are configured such that the bladder expels substantially all of the contents of the bladder through the injection needle.

3. The medical fluid injection device of claim 1 in which the bladder and pre-stress member are configured such that most of the liquid in the bladder is expelled at a substantially constant flow rate.

4. The medical fluid injection device of claim 1 in which the pre-stress member is generally elongated and has a length within the bladder greater than a length of the bladder in a non-pressurized condition.

5. The medical fluid injection device of claim 1 in which the pre-stress member has an outer diameter within the bladder larger than an inner diameter of the bladder in a non-pressurized condition.

6. The medical fluid injection device of claim 5 in which the pre-stress member has a length within the bladder greater than the length of the bladder in a non-pressurized condition.

7. The medical fluid injection device of claim 1 wherein the skin-facing surface includes a skin-contacting protrusion located around the injection needle when in the injection position.

8. The medical fluid injection device of claim 1 further comprising a double sided adhesive member adhered on one side to the skin-facing surface, the other side of the adhesive member including a removable cover that may be removed to expose adhesive for holding the medical fluid injection device on the skin of a patient.

9. The medical fluid injection device of claim 8 in which the double sided adhesive member includes a releasable portion that remains adhered to the patient's skin upon removal of the medical fluid injection device.

10. The medical fluid injection device of claim 1 further comprising a double-sided adhesive member adhered on one side to the skin-facing surface, the other side of the adhesive member including a removable cover that may be removed to expose adhesive for holding the medical fluid injection device on the skin of a patient.

11. The medical fluid injection device of claim 10 in which the double sided adhesive member includes a releasable portion that remains adhered to the patient's skin upon removal of the medical fluid injection device.

12. The medical fluid injection device of claim 10 in which the double sided adhesive member extends fully around the injection needle.

13. The medical fluid injection device of claim 10 in which the double sided adhesive member comprises double sided tape.

* * * * *